US008105232B2

United States Patent
Yamazaki

(10) Patent No.: US 8,105,232 B2
(45) Date of Patent: Jan. 31, 2012

(54) FLUORESCENT ENDOSCOPIC DEVICE AND METHOD OF CREATING FLUORESCENT ENDOSCOPIC IMAGE

(75) Inventor: Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 373 days.

(21) Appl. No.: 12/394,757

(22) Filed: Feb. 27, 2009

(65) Prior Publication Data

US 2009/0216085 A1 Aug. 27, 2009

(30) Foreign Application Priority Data

Feb. 27, 2008 (JP) ................................. 2008-046648

(51) Int. Cl.
*A61B 1/06* (2006.01)
*A61B 5/05* (2006.01)

(52) U.S. Cl. ........................................ 600/160; 600/407

(58) Field of Classification Search .................. 600/160, 600/407, 476, 478, 178, 180, 324, 431, 175; 345/77, 589; 359/212.1, 213.1; 250/227.26
See application file for complete search history.

(56) References Cited

U.S. PATENT DOCUMENTS

| | | | | |
|---|---|---|---|---|
| 5,647,368 A * | 7/1997 | Zeng et al. | ...................... | 600/476 |
| 6,293,911 B1 | 9/2001 | Imaizumi et al. | | |
| 6,433,345 B1 * | 8/2002 | Hayashi et al. | ............ | 250/458.1 |
| 7,283,858 B2 * | 10/2007 | Sendai | ........................... | 600/407 |
| 2001/0049473 A1 | 12/2001 | Hayashi | | |
| 2002/0085753 A1 * | 7/2002 | Sendai | ........................... | 382/168 |
| 2003/0078477 A1 * | 4/2003 | Kang et al. | ..................... | 600/178 |
| 2003/0135092 A1 * | 7/2003 | Cline et al. | ..................... | 600/160 |
| 2003/0191368 A1 * | 10/2003 | Wang et al. | ..................... | 600/160 |

FOREIGN PATENT DOCUMENTS

JP 2001-314366 11/2001

* cited by examiner

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

An inter-image calculation portion includes a switch circuit made up of three switch portions for switching each of three image data (R, G, B) from a 3-board processing portion, a first divider, a second divider, a first adder, a second adder, a first LUT, a second LUT, a first clip portion, and a second clip portion. The inter-image calculation portion executes addition processing of two different fluorescent images with two different wavelength bands and division processing the two different fluorescent images with two different wavelength bands and then it executes addition processing which adds the addition results and the division results of the two different fluorescent images with two different wavelength bands or it executes subtraction processing which subtracts the addition results from the division results of the two different fluorescent images with two different wavelength bands.

13 Claims, 15 Drawing Sheets

| R | G | R | G |
|---|---|---|---|
| G | B | G | B |
| R | G | R | G |
| G | B | G | B |

FLUORESCENT ENDOSCOPIC DEVICE AND METHOD OF CREATING FLUORESCENT ENDOSCOPIC IMAGE

This application claims benefit of Japanese Application No. 2008-046648 filed in Japan on Feb. 27, 2008, the contents of which are incorporated herein by this reference.

BACKGROUND OF THE INVENTION

1. Field of the Invention

The present invention relates to a fluorescent endoscopic device and a method of creating a fluorescent endoscopic image for diagnosing a normal tissue and a lesion tissue by obtaining a reflection light image and a fluorescent image.

2. Description of the Related Art

Recently, endoscopes have been widely used in the medical field and the industrial field. Particularly, in the medical field, proposals have been made on technologies for obtaining an image in which a normal tissue and a lesion tissue can be easily discriminated in addition to endoscopic devices for obtaining usual images by usual white light.

For example, using a nature that a normal tissue and a lesion tissue emit different fluorescent intensity of auto-fluorescence if excitation light in an excited wavelength region of a biologically-inherent fluorescent substance is irradiated to a living tissue, such a technology is proposed that local existence of a lesion tissue and an infiltrated range are displayed as fluorescent images by irradiating the excitation light in a predetermined wavelength region to the living tissue and by receiving fluorescent light emitted from the biologically-inherent fluorescent substance.

Since the fluorescent intensity from the living tissue is extremely weak, S/N of the measured fluorescent image is extremely low. Therefore, if standardized calculation is carried out using such a fluorescent image, the S/N of a calculated image on the basis of an obtained calculation value also becomes extremely low, and discrimination between a normal tissue and a lesion tissue becomes extremely difficult.

Then, in Japanese Patent Application Laid-Open Publication No. 2001-314366 and the like, for example, with a purpose of improving S/N and contrast when a calculated image is created by carrying out the standardized calculation on the basis of a ratio between two types of fluorescent images, a device for adding an offset value to each image, respectively, before the standardized calculation is disclosed.

SUMMARY OF THE INVENTION

A fluorescent endoscopic device of the present invention includes an irradiation portion for irradiating illumination light and excitation light to a subject, a light receiving portion for receiving a reflection light image generated from the subject on the basis of the illumination light and a first fluorescent image and a second fluorescent image generated from the subject on the basis of the excitation light, a calculation portion for executing processing of adding a result of addition processing of the first fluorescent image and the second fluorescent image and a result of division processing of the first fluorescent image and the second fluorescent image, and an image creation portion for creating a fluorescent observation image on the basis of the reflection light image by means of the illumination light, the first fluorescent image, the second fluorescent image and calculation results of the calculation portion.

A method of creating a fluorescent endoscopic image of the present invention includes steps of irradiating illumination light and excitation light from an irradiation portion, receiving a reflection light image on the basis of the illumination light and a first fluorescent image and a second fluorescent image on the basis of the excitation light, executing calculation processing of adding a result of addition processing of the first fluorescent image and the second fluorescent image and a result of division processing of the first fluorescent image and the second fluorescent image, and creating a fluorescent observation image on the basis of the reflection light image by means of the illumination light, the first fluorescent image, the second fluorescent image, and a calculation result of the calculation processing.

DETAILED DESCRIPTION OF THE PREFERRED EMBODIMENTS

Embodiments of the present invention will be described below referring to the attached drawings.

Embodiment 1

Figure 1:
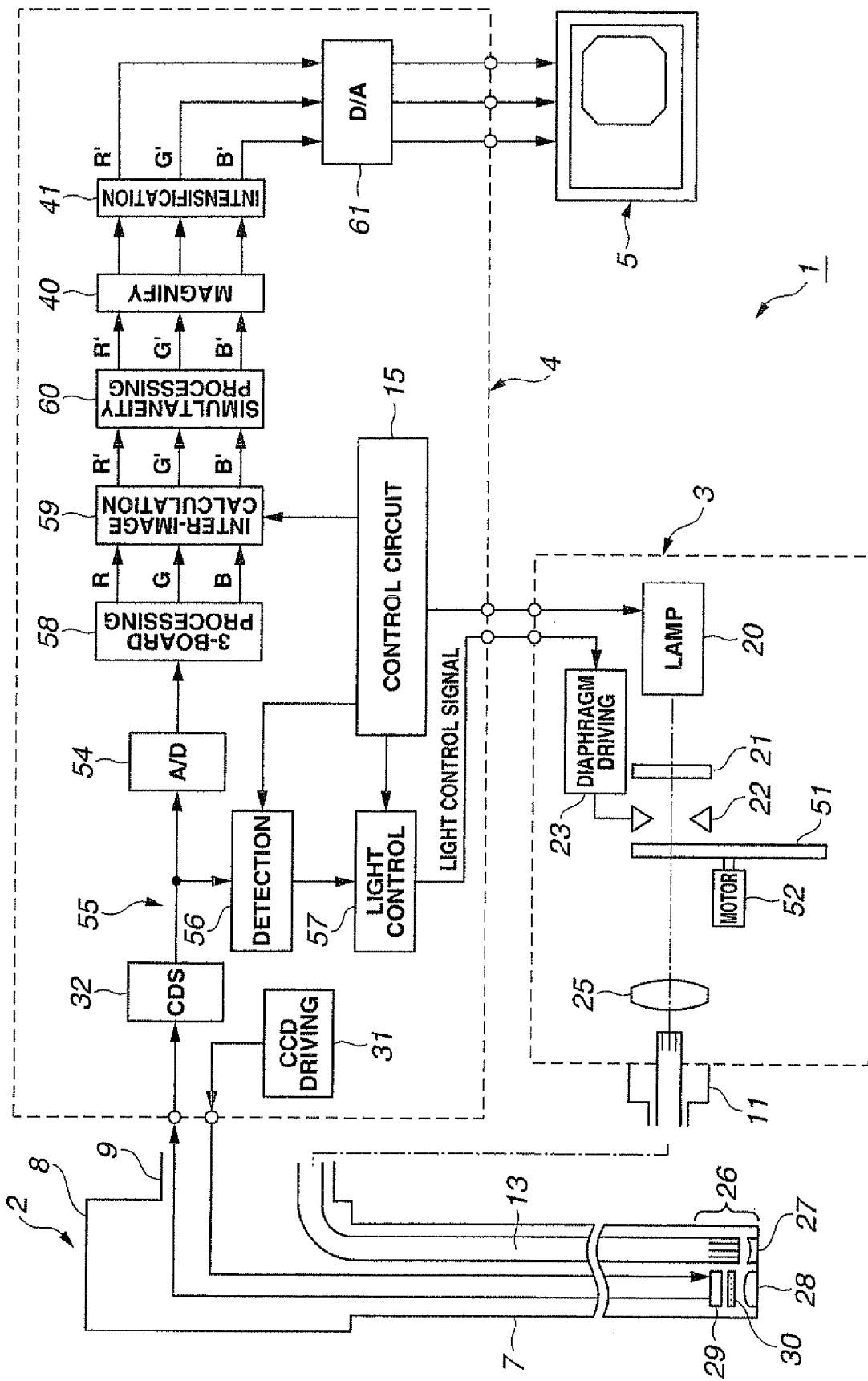
FIG. 1 is a configuration diagram illustrating configuration of a fluorescent endoscopic device according to an embodiment I of the present invention.
Figure 2:
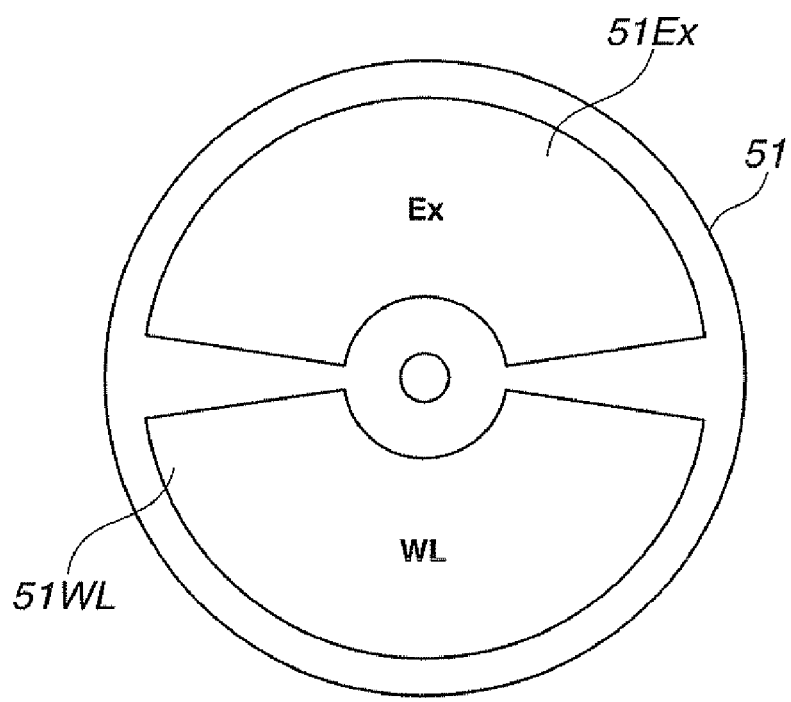
FIG. 2 is a diagram illustrating configuration of a rotating filter in FIG. 1.
Figure 3:
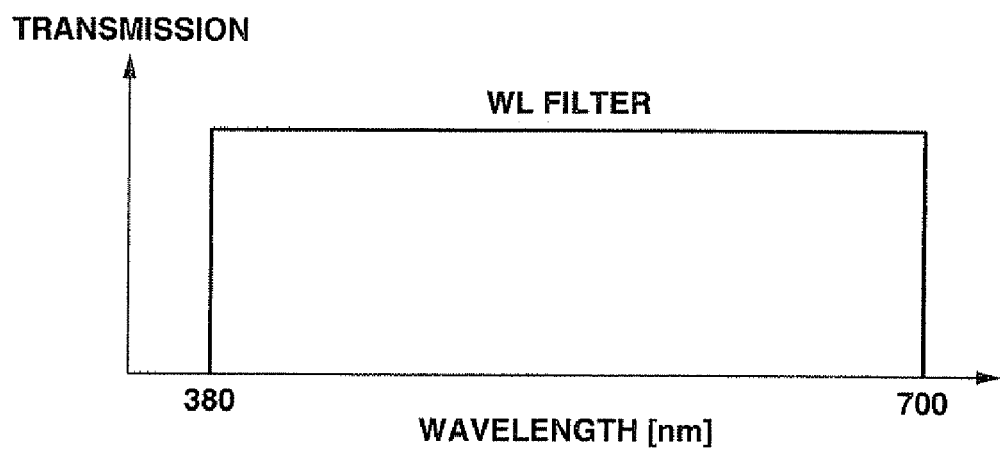
FIG. 3 is a diagram illustrating a transmission characteristic of a WL filter in FIG. 2.
Figure 4:
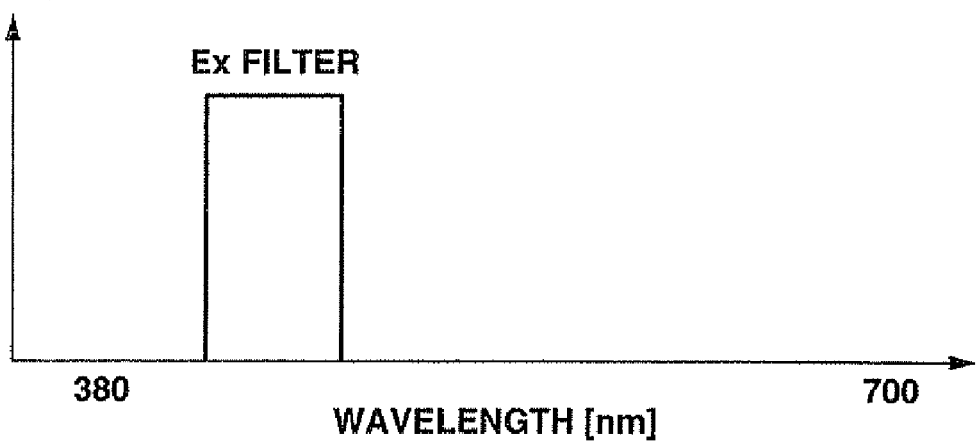
FIG. 4 is a diagram illustrating a transmission characteristic of an EX filter in FIG. 2.
Figure 5:
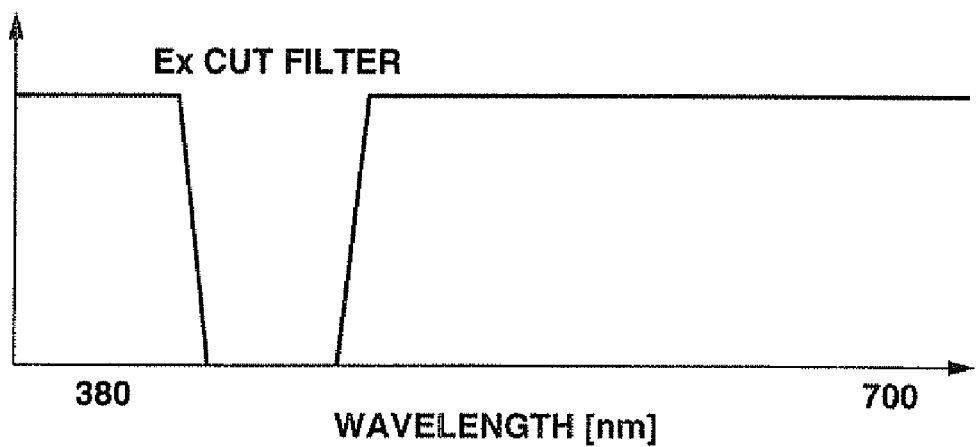
FIG. 5 is a diagram illustrating a transmission characteristic of excitation light cut filter in FIG. 1.
Figures 6, 7:
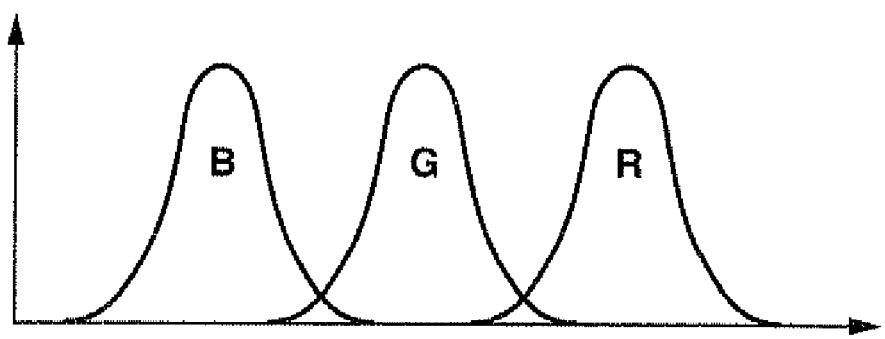
FIG. 6 is a diagram illustrating a Bayer-arrayed color filter arranged on an image pickup face of a CCD in FIG. 1.
FIG. 7 is a diagram illustrating a transmission characteristic of the color filter in FIG. 6.
Figure 8:
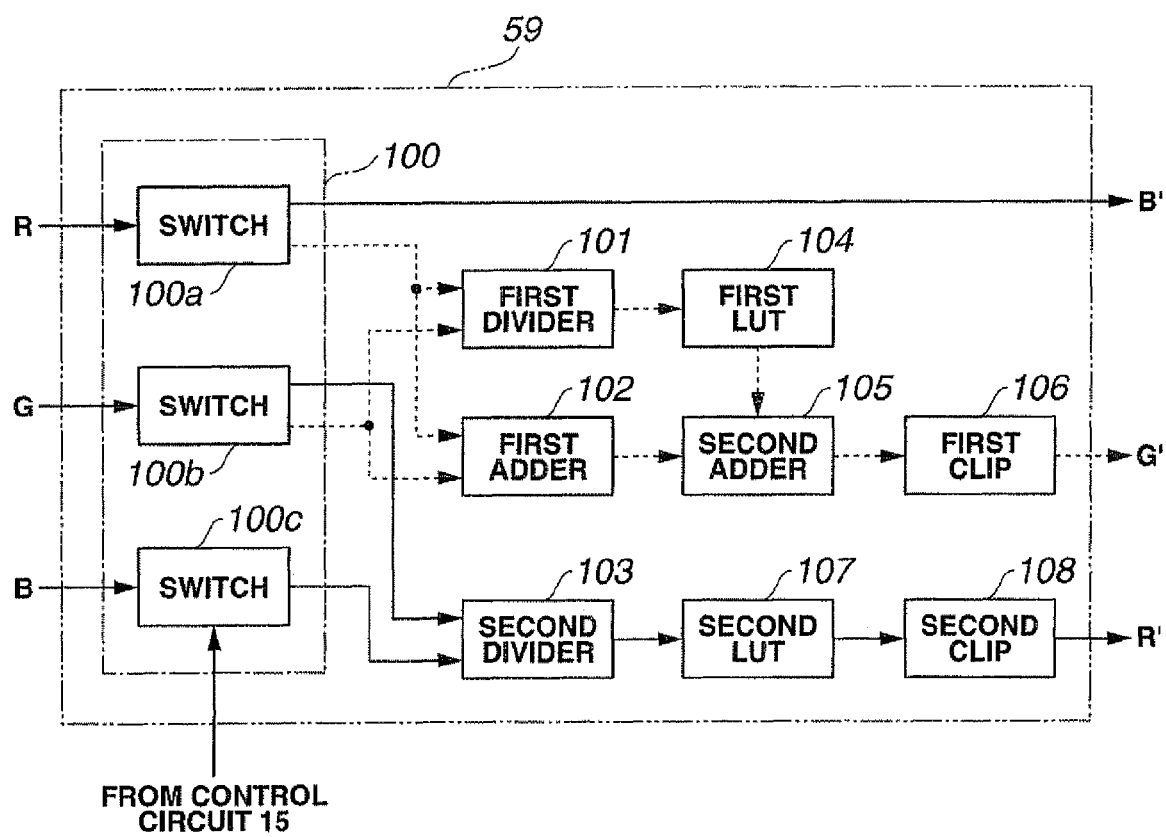
FIG. 8 is a block diagram illustrating configuration of an inter-image calculation portion in FIG. 1.
Figure 9:
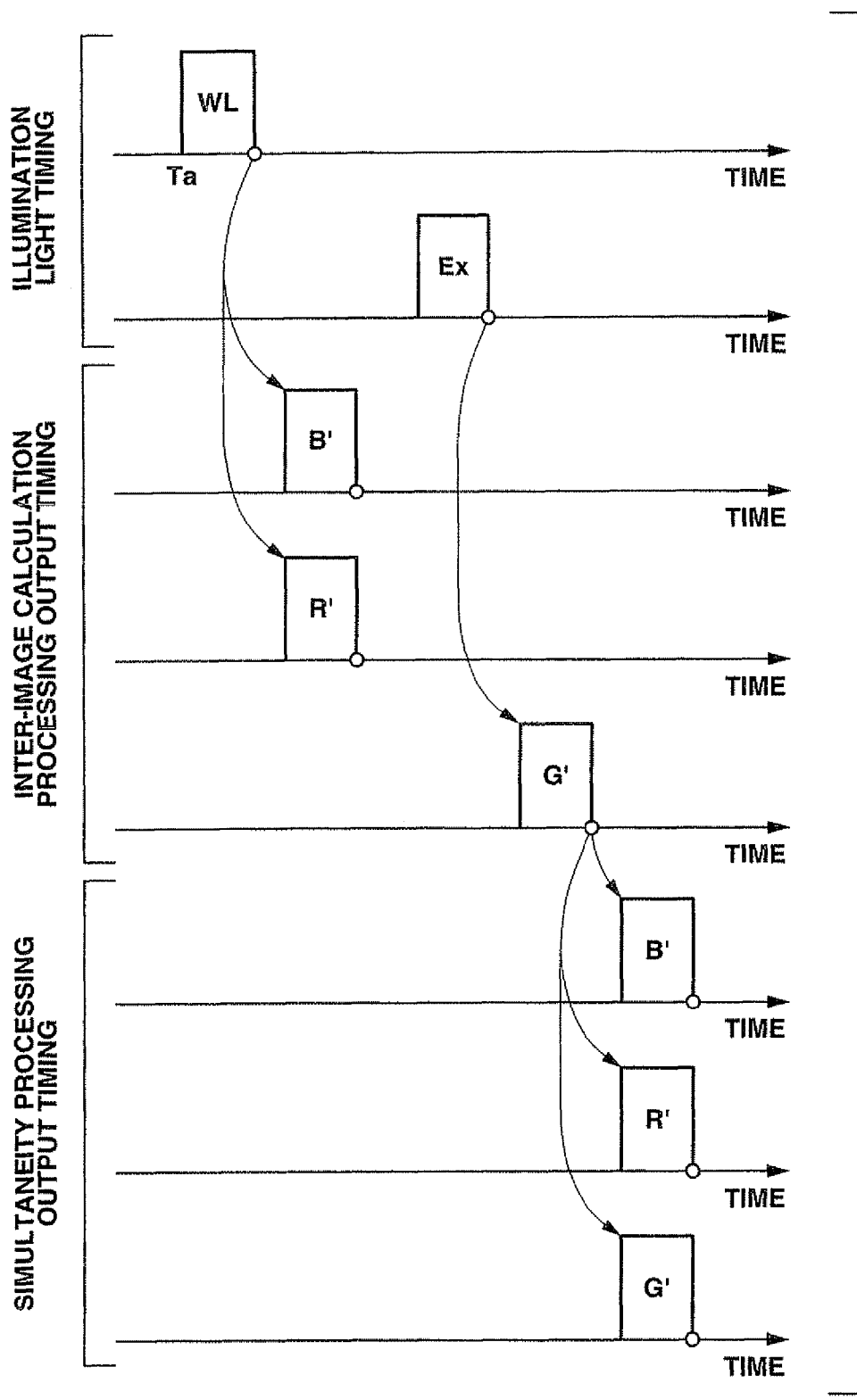
FIG. 9 is a diagram illustrating timing of image data of the inter-image calculation portion and a simultaneity portion in FIG. 1.
Figure 10:
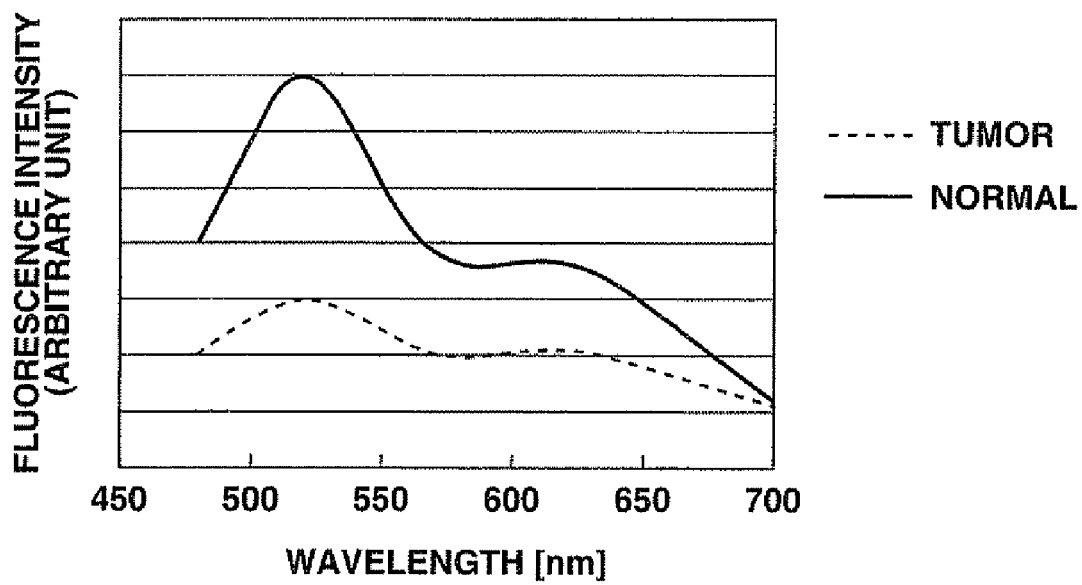
FIG. 10 is a first spectral diagram illustrating intensity distribution of a fluorescent spectrum of auto-fluorescence for explaining an action of the inter-image calculation portion in FIG. 8.
Figure 11:
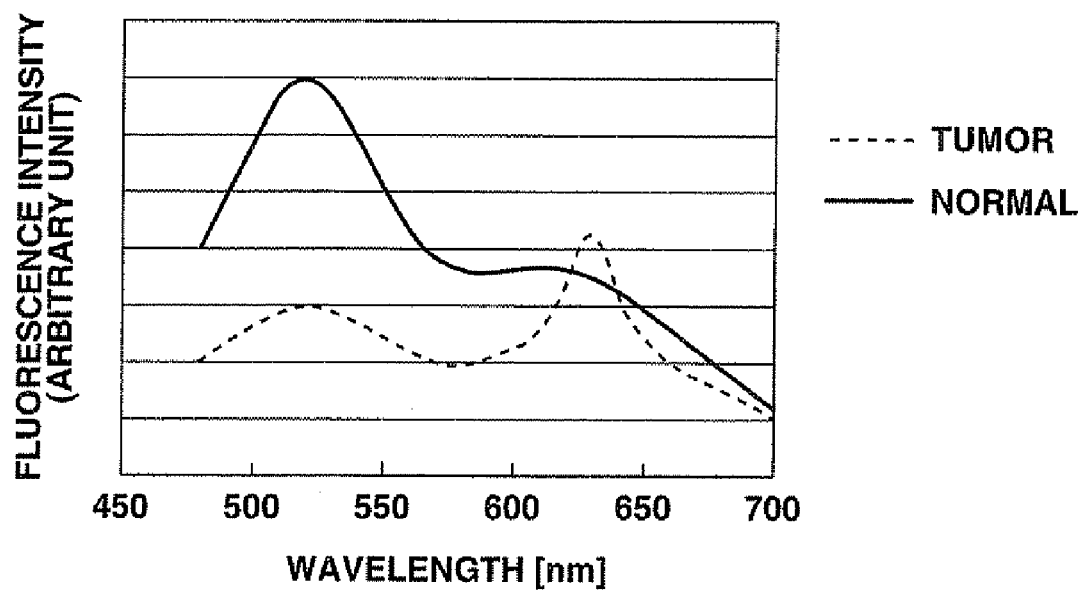
FIG. 11 is a second spectral diagram illustrating intensity distribution of a fluorescent spectrum of auto-fluorescence for explaining an action of the inter-image calculation portion in FIG. 8.
Figure 12:
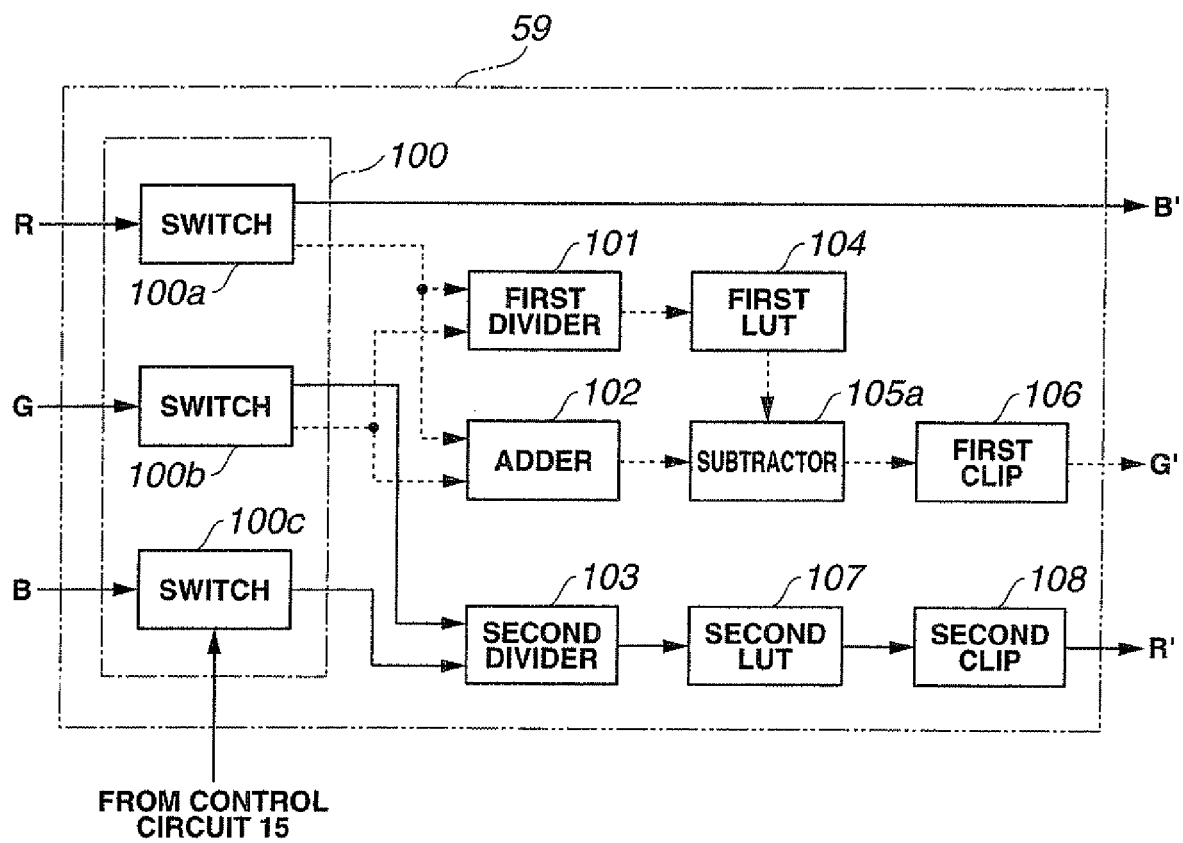
FIG. 12 is a block diagram illustrating configuration of a variation of the inter-image calculation portion in FIG. 8.

FIGS. 1 to 12 relate to an embodiment 1 of the present invention, in which FIG. 1 is a configuration diagram illustrating configuration of a fluorescent endoscopic device, FIG. 2 is a diagram illustrating configuration of a rotating filter in FIG. 1, FIG. 3 is a diagram illustrating a transmission characteristic of a WL filter in FIG. 2, FIG. 4 is a diagram illustrating a transmission characteristic of an EX filter in FIG. 2, FIG. 5 is a diagram illustrating a transmission characteristic of excitation light cut filter in FIG. 1, FIG. 6 is a diagram illustrating a Bayer-arrayed color filter arranged on an image pickup face of a CCD in FIG. 1, FIG. 7 is a diagram illustrating a transmission characteristic of the color filter in FIG. 6, FIG. 8 is a block diagram illustrating configuration of an inter-image calculation portion in FIG. 1, FIG. 9 is a diagram illustrating timing of image data of the inter-image calculation portion and a simultaneity portion in FIG. 1, FIG. 11 is a first spectral diagram illustrating intensity distribution of a fluorescent spectrum of auto-fluorescence for explaining an action of the inter-image calculation portion in FIG. 8, FIG. 11 is a second spectral diagram illustrating intensity distribution of a fluorescent spectrum of auto-fluorescence for explaining an action of the inter-image calculation portion in FIG. 8, and FIG. 12 is a block diagram illustrating configuration of a variation of the inter-image calculation portion in FIG. 8.

As shown in FIG. 1, a fluorescent endoscopic device 1 of the present embodiment 1 is provided with an electronic endoscope 2 (hereinafter abbreviated simply as an endoscope) inserted into a body cavity and the like for conducting an endoscopic examination, a light-source device 3 for supplying illumination light to the endoscope 2, a video processor 4 for driving an image pickup portion built in the endoscope 2 and for carrying out signal processing for an output signal of the image pickup portion, and a monitor 5 for displaying an endoscopic image picked up by the image pickup portion when a video signal outputted from the video processor 4 is inputted.

The endoscope 2 has an elongated insertion portion 7, an operation portion 8 provided at a rear end of the insertion portion 7, and a universal cable 9 extended from the operation portion 8, and a light guide connector 11 at an end portion of the universal cable 9 is detachably connected to the light-source device 3, while a signal connector (not shown) provided also at the end portion of the universal cable 9 is detachably connected to the video processor 4.

A light guide 13 for transmitting illumination light is inserted through the insertion portion 7, and by connecting the light guide connector 11 at the end portion on the hand side in the light guide 13 to the light-source device 3, the illumination light from the light-source device 3 is supplied to the light guide 13.

The light-source device 3 incorporates a lamp 20 generating the illumination light, and the lamp 20 generates the illumination light covering a wavelength region of (red, green, blue and the like) visible light. The illumination light has infrared light cut off by an infrared cut filter 21 to be made into substantially white illumination light and then, is made to enter a diaphragm 22. The diaphragm 22 has the opening amount thereof controlled by a diaphragm driving circuit 23. Then, an illumination light amount passing through the diaphragm 22 is controlled.

The illumination light having passed through the diaphragm 22 enters a focusing lens 25 through a rotating filter 51 made up of a WL filter 51 WL (transmission characteristics thereof are shown in FIG. 3) transmitting white light generating the illumination light as shown in FIG. 2 and an EX filter 51 EX (transmission characteristics thereof are shown in FIG. 4) transmitting excitation light, the light is focused by the focusing lens 25 and enters an end face on the hand side of the light guide 13, that is, an incident end face. The rotating filter 51 is rotated by a motor 52 at a constant speed.

The illumination light from the light guide 13 is transmitted by the light guide 13 to the distal end face thereof and outputted to the outside through an illumination lens 27 mounted at an illumination window provided at a distal end portion 26 of the insertion portion 7 for illuminating a surface of the living tissue such as an affected part and the like in the body cavity.

An observation window is provided adjacently to the illumination window at the distal end portion 26, and an objective lens 28 is mounted on the observation window. The objective lens 28 forms an optical image by return light from the living tissue. A color charge coupling device (hereinafter abbreviated as CCD) 29 as a solid image pickup device is arranged at an image forming position of the objective lens 28, and the optical image is photoelectrically converted by the CCD 29. An excitation light cut filter 30 (transmission characteristics thereof are shown in FIG. 5) for cutting off the excitation light is provided on the image pickup face of the CCD 29.

The CCD 29 is connected to one end of a signal line, and by connecting a signal connector having the other end of the signal line connected, to the video processor 4, connection is made to a CCD driving circuit 31 and a CDS circuit 32 in the video processor 4. The CCD 29 photoelectrically converts the optical image by application of a CCD driving signal from the CCD driving circuit 31. An image pickup signal from the CCD 29 obtained by photoelectric conversion is inputted to the CDS circuit 32 and CDS-processed (a signal component is extracted from the image pickup signal and converted into a base band signal).

An output signal of the CDS circuit 32 is inputted to an A/D conversion circuit 54 and converted into a digital signal and also inputted to a light control circuit 57 via a detection circuit 56 constituting a light control signal creation circuit 55. The light control circuit 57 creates a light control signal and controls the diaphragm driving circuit 23 of the light-source device 3.

The digital signal created by the A/D conversion circuit 54 is converted by a 3-board processing portion 58 to three image data (R, G, B), The image data (R, G, B) are given calculation processing, which will be described later, by an inter-image calculation portion 59. The inter-image calculation portion 59 creates three image data (R', G', B') from the three image data (R, G, B) and outputs them to a simultaneity portion 60. The simultaneity portion 60 synchronizes output timing of the three image data (R', G', B') created by the inter-image calculation portion 59.

The 3-board processing portion 58 separates the image pickup signal through a color filter (transmission characteristics thereof are shown in FIG. 7), which are Bayer-arrayed shown in FIG. 6 and arranged in the CCD 29 on the image pickup face, into an RGB color image signal and converts it into the three image data (R, G, B) and outputs it to the inter-image calculation portion 59 as images of an R channel, a G channel, and a B channel. Details of the inter-image calculation portion 59 and the simultaneity portion 60 will be described later.

The three image data (R', G', B') synchronized by the simultaneity portion 60 is inputted into a magnification circuit 40 and given magnification interpolation processing. An output signal of the magnification circuit 40 is inputted into an intensification circuit 41 and given sharpening processing such as structural intensification and the like. Furthermore, after the magnification interpolation processing and the intensification processing, the image data (R', G', B') is converted by a D/A conversion circuit 61 to an analog signal and outputted from an output end to the monitor 5.

In the video processor 4, the detection circuit 56, the light control circuit 57, and the inter-image calculation portion 59 are controlled by a control circuit 15. The control circuit 15 also drives and controls lighting control of the lamp 20 in the light-source device and the motor 52 in addition to the control of the detection circuit 56, the light control circuit 57, and the inter-image calculation portion 59.

The inter-image calculation portion 59 includes, as shown in FIG. 8, a switch circuit 100 constituted by three switch portions 100a, 100b, 100c for switching each of the three image data (R, G, B) from the 3-board processing portion 58, a first divider 101, a second divider 103, a first adder 102, a second adder 105, a first lookup table (LUT) 104, a second LUT 107, a first clip portion 106, and a second clip portion 108.

The three switch portions 100a, 100b, 100c of the switch circuit 100 are switches for switching each of the three image data (R, G, B) from the 3-board processing portion 58 on the basis of control from the control circuit 15.

An action of the present embodiment constituted as above will be described. The inter-image calculation portion 59 switches the switch portions 100a, 100b, 100c according to illumination timing on the basis of the control signal from the control circuit 15. The inter-image calculation portion 59 executes calculations shown in the following formula (1) for the image data (R, G, B) outputted through the switch portions 100a, 100b, 100c at each of the first divider 101, the second divider 103, the first adder 102, the second adder 105, the first LUT 104, the second LUT 107, the first clip portion 106, and the second clip portion 108 and outputs as the image data (R', G', B').

$R' = K \log_2(G_{wl}/B_{wl})$ $G' = G_{ex} + R_{ex} + K \log_2(G_{ex}/R_{ex})$ $B'R_{wl}$ (1)

Specifically, as shown in FIG. 9, the switch circuit 100 switches the switch portions 100a, 100b, 100c according to the illumination timing of the excitation light when the excitation light is illuminated through the Ex filter 51 Ex of the rotating filter 51 by means of control of the control circuit 15 and outputs the R image data (hereinafter referred to as $R_{ex}$) from the R channel of the 3-board processing portion 58 when the excitation light is irradiated to the first divider 101 and the first adder 102. Similarly, the switch circuit 100 outputs the G image data (hereinafter referred to as $G_{ex}$) from the G channel of the 3-board processing portion 58 when the excitation light is irradiated to the first divider 101 and the first adder 102.

The first divider 101 executes calculation of "$G_{ex}/R_{ex}$" for each pixel. At the subsequent first LUT 104, calculation of logarithmic arithmetic and multiplication of a coefficient K to the output of the first divider 101 is executed by referring to a table.

Here, the coefficient K is 16, for example, if the image data is made up of 8 bits, for example, and a value of K $\log_2 (G_{ex}/R_{ex})$ is kept to 8 bits. A predetermined value may be set by the number of bits, excitation wavelength and the like. Moreover, switching by means of a scope SW (not shown) and the like may be possible by making a plurality of coefficient value sets selectable.

The first adder 102 adds $R_{ex}$ and $G_{ex}$, while the subsequent second adder 105 adds an output of the first LUT 104 to an output of the first adder 102.

Furthermore, the first clip portion 106 executes clip processing to an output of the second adder 105 in the case where predetermined bit accuracy is exceeded and outputs the result as the image data G', which is a G channel output of the inter-image calculation portion 59, to the simultaneity portion 60.

On the other hand, when white light is irradiated through the WL filter 51 WL of the rotating filter 51, the switch circuit 100 switches the switch portions 100a, 100b, 100c according to the illumination timing of the white light by means of control of the control circuit 15 and outputs the R image data when the white light is irradiated (hereinafter referred to as $R_{wl}$) as the image data B', which is a B-channel output of the inter-image calculation portion 59, to the simultaneity portion 60. Also, the switch circuit 100 switches the switch portions 100a, 100b, 100c according to the illumination timing of the white light and outputs the G image data (hereinafter referred to as $G_{wl}$) from the G channel of the 3-board processing portion 58 at the illumination of the white light and the B image data (hereinafter referred to as $B_{wl}$) from the B channel to the second divider 103, and the second divider 103 executes calculation of "$G_{wl}/R_{wl}$" for each pixel. At the subsequent second LUT 107, calculation as multiplication of logarithmic arithmetic and the coefficient K to the output of the second divider 103 is executed by referring to a table.

The second clip portion 108 executes clip processing to an output of the second LUT 107 in the case where predetermined bit accuracy is exceeded and outputs the result as the image data R', which is an R-channel output of the inter-image calculation portion 59, to the simultaneity portion 60.

The simultaneity portion 60 synchronizes the image data G', the image data B', the image data R' outputted by the above calculation at the inter-image calculation portion 59 and outputs the result as the image data (R', G', B') to the magnification circuit 40.

If the excitation light is irradiated in a usual case, in the spectral diagram shown in FIG. 10, strong fluorescent light is emitted from a normal tissue as shown by a solid line, while weak fluorescent light is emitted from a lesion tissue as shown by a broken line, and thus, it can be determined if the living tissue is normal or in a lesion state by measuring the fluorescent intensity. Also, a fluorescent spectrum generated from the lesion tissue might emit spectrum as shown in FIG. 11, which is different from FIG. 10, depending on the lesion tissue.

An effect of the division in the formula (1) will be explained. In general, a pixel value IntF(i, j) at a position (i, j) of a fluorescent image is defined by the formula (2):

$$IntF(i, j) = IntEx(i, j)\sum_{\lambda} Obj(\lambda, i, j)Sens(\lambda) \quad (2)$$

where

IntEx(i, j) is intensity at the position (i, j) of the excitation light,

Obj($\lambda$, i, j) is a comprehensive response characteristic of a mucous considering concentrations and fluorescence quantum yield of endogenous fluorescent substances and dispersion and absorbing characteristics of the excitation light and the fluorescence, Sens ($\lambda$) is a comprehensive spectral product of an image pickup system in which spectral transmittance of the objective lens and a spectral sensitivity of the image pickup device are combined, and $\lambda$ is a fluorescence detection wavelength band.

If the fluorescence detection wavelength band $\lambda$ of the fluorescence is a first band Band-1, a second band Band-2, it is represented by the formula (3), respectively. In the formula (3), Obj($\lambda$, i, j) is the response characteristic according to the detection wavelength band $\lambda$.

$$IntF_{band-1}(i, j) = IntEx(i, j) \sum_{\lambda\_band-1} Obj(\lambda, i, j)Sens(\lambda) \quad (3)$$

$$IntF_{band-2}(i, j) = IntEx(i, j) \sum_{\lambda\_band-2} Obj(\lambda, i, j)Sens(\lambda)$$

Therefore, the term of the illumination intensity of the excitation light can be cancelled by acquiring a ratio between $IntF_{band-1}$ and $IntF_{band-2}$ as in the formula (4).

$$\frac{IntF_{band-1}(i, j)}{IntF_{band-2}(i, j)} = \frac{\sum_{\lambda\_band-1} Obj(\lambda, i, j)Sens(\lambda)}{\sum_{\lambda\_band-2} Obj(\lambda, i, j)Sens(\lambda)} \quad (4)$$

Subsequently, an effect of the logarithmic arithmetic in the formula (1) will be explained. Since the ratio "$G_{ex}/R_{ex}$" between the fluorescent image data $R_{ex}$ picked up by the R channel of the CCD 29 and $G_{ex}$ by the G channel of the CCD 29 becomes 1 or more in the case of the fluorescent spectrum in FIG. 10, the logarithmic component of the formula (1) becomes a positive value. On the other hand, it is "$G_{ex}/R_{ex}$"<1 (less than 1) in FIG. 11, which is a negative value. That is, a contrast change can be added onto the image data to which $R_{ex}$ and $G_{ex}$ are added according to the size of $R_{ex}$ and $G_{ex}$ by acquiring logarithm. In the logarithmic arithmetic, it is possible to keep an output value low against a large input value, and G' in the formula (1) can keep the dynamic range thereof appropriate only by the division as compared with a case in which the logarithm is not acquired.

Thus, image information reflecting a spectral shape can be created by means of the logarithmic arithmetic.

As mentioned above in the present embodiment, since the above-mentioned calculation is carried out in the inter-image calculation portion 59, brightness of the fluorescent image is improved so that the drop in S/N can be alleviated and the image information reflecting the spectral shape can be created.

That is, the result of the addition processing of the first fluorescent image $R_{ex}$ and the second fluorescent image $G_{ex}$ improves the S/N and the result of the logarithmic arithmetic after the division processing of the first fluorescent image $R_{ex}$ and the second fluorescent image $G_{ex}$ reflects the spectral shape, and the fluorescent observation image with alleviated S/N drop can be created by carrying out the addition of the two results.

(Variation)

As a variation of the inter-image calculation portion 59 of the embodiment 1, as shown in FIG. 12, configuration may use a subtractor 105a instead of the second adder 105. The calculation by the inter-image calculation portion 59 in this case will be as in the formula (5);

$$R'=K\log_2(G_{wl}/B_{wl})$$

$$G'=G_{ex}+R_{ex}-K\log_2(R_{ex}/G_{ex})$$

$$B'=r_{wl} \quad (5)$$

In the variation, too, the actions/effects similar to the present embodiment can be obtained.

Embodiment 2

Figure 13:
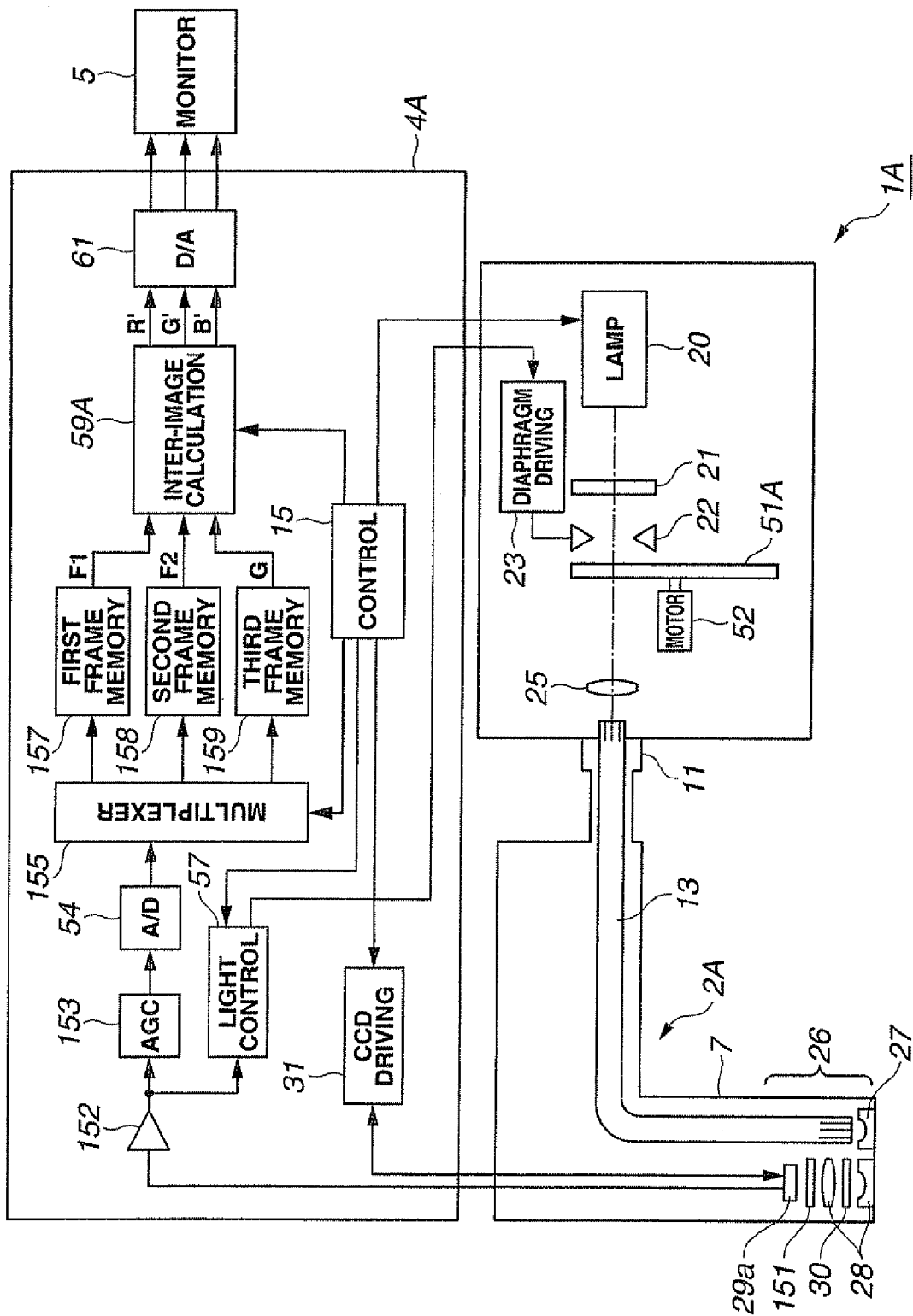
FIG. 13 is a configuration diagram illustrating configuration of a fluorescent endoscopic device according to an embodiment 2 of the present invention.
Figure 14:
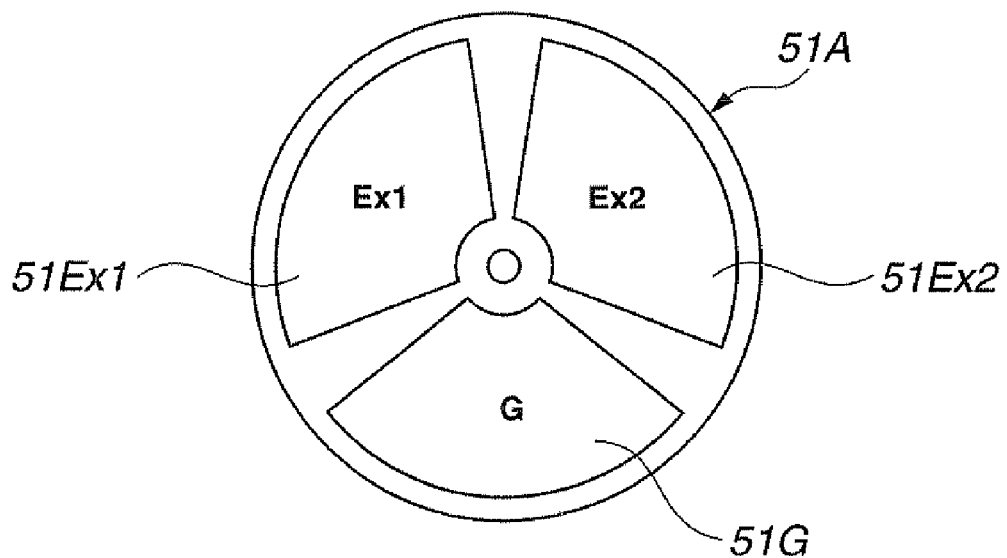
FIG. 14 is a diagram illustrating configuration of the rotating filter in FIG. 13.
Figure 15:
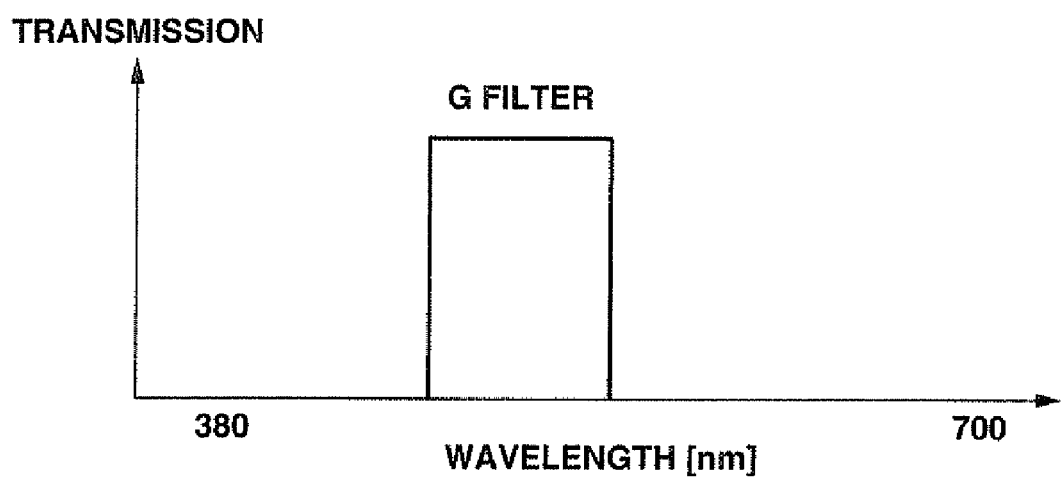
FIG. 15 is a diagram illustrating a transmission characteristic of a G filter in FIG. 14.
Figure 16:
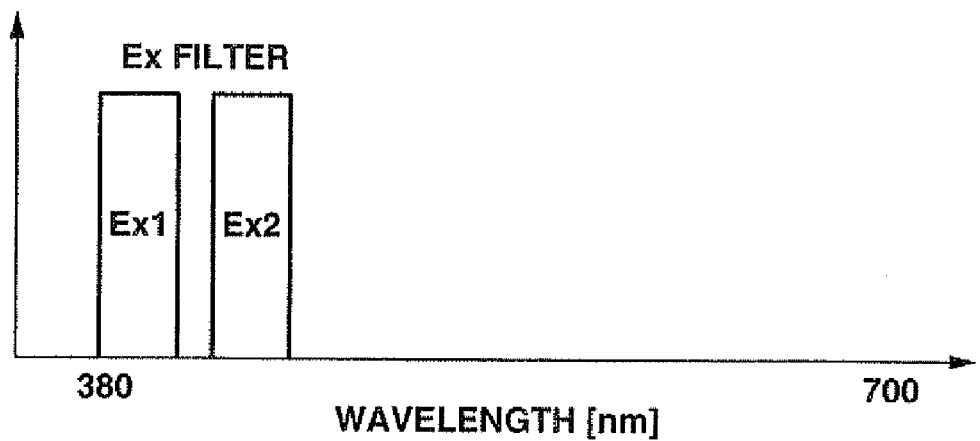
FIG. 16 is a diagram illustrating a transmission characteristic of an EX1 filter and an EX2 filter in FIG. 14.
Figure 17:
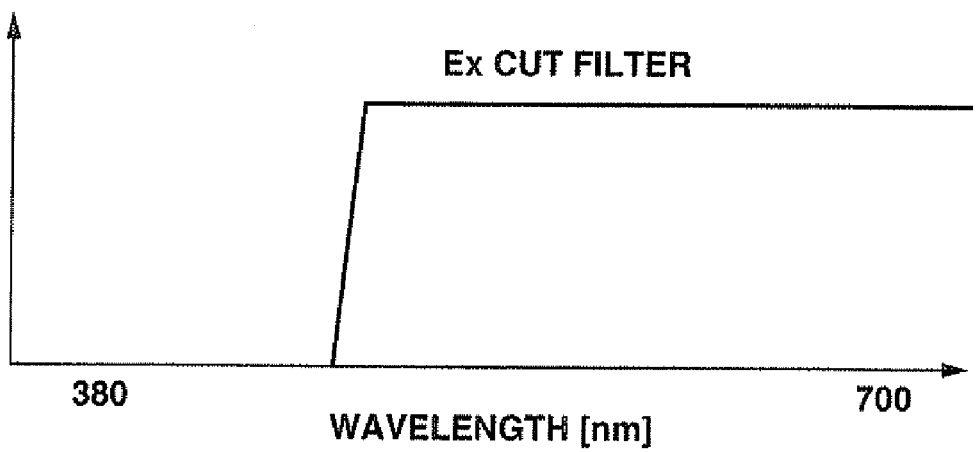
FIG. 17 is a diagram illustrating a transmission characteristic of an excitation light cut filter in FIG. 13.
Figure 18:
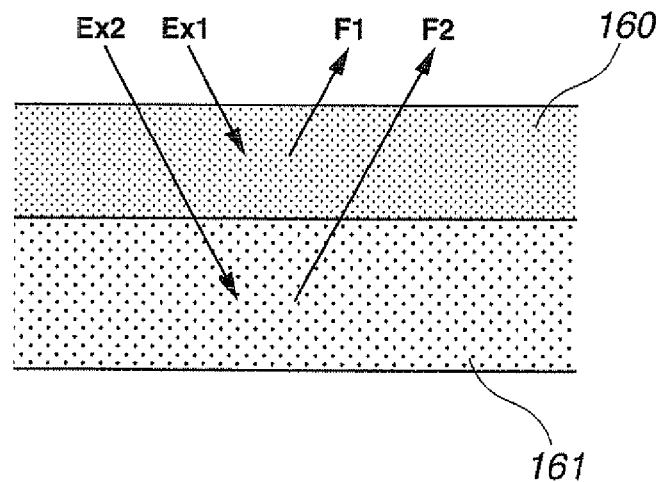
FIG. 18 is a diagram for explaining an action of a fluorescent endoscopic device in FIG. 13.
Figure 19:
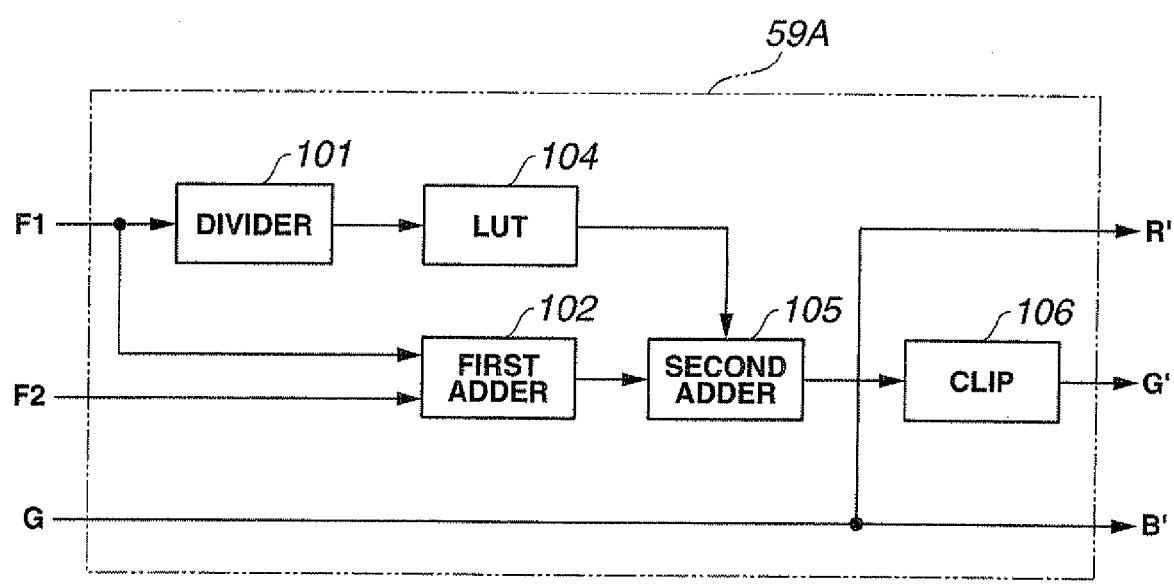
FIG. 19 is a block diagram illustrating configuration of an inter-image calculation portion in FIG. 13.
Figure 20:
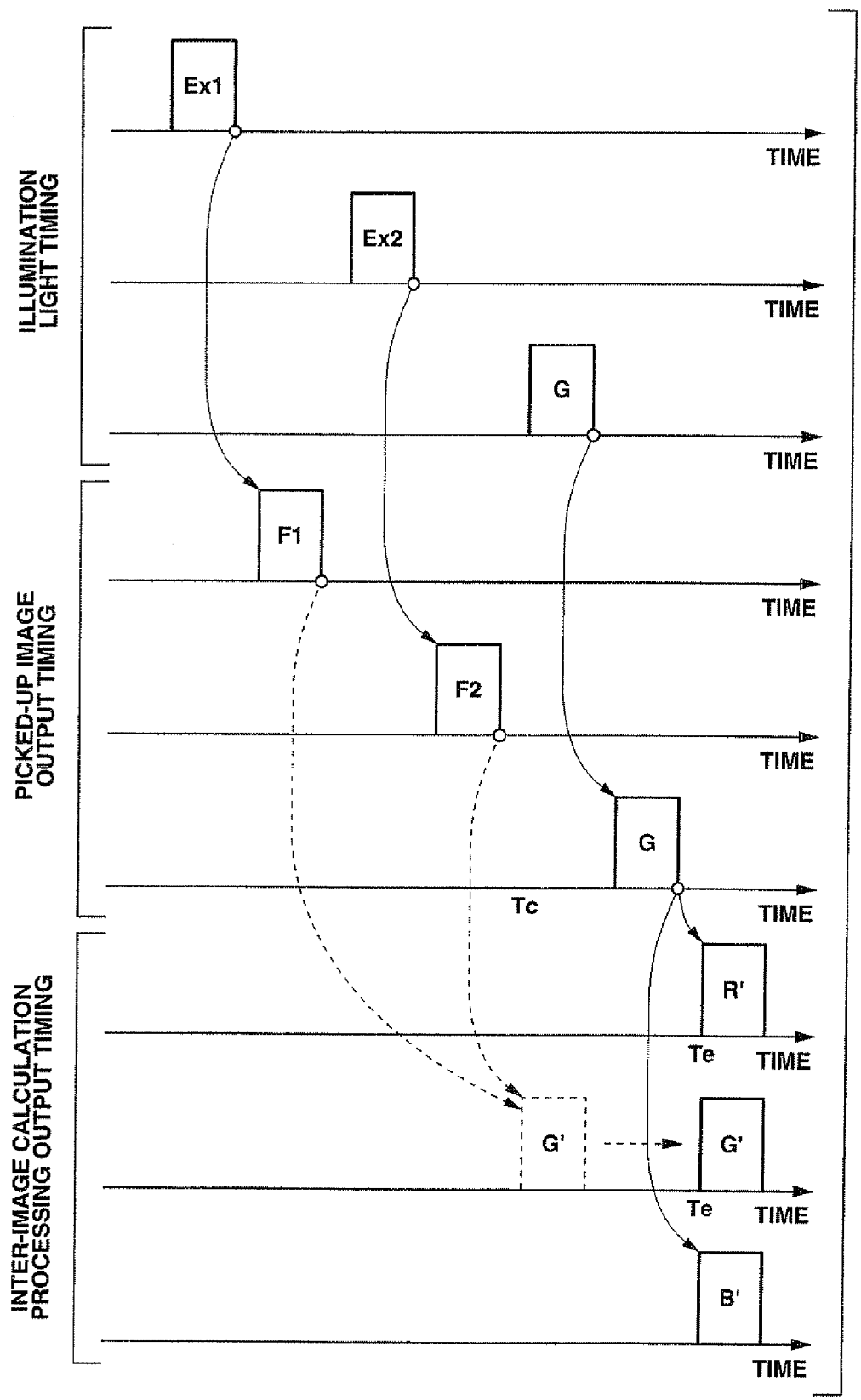
FIG. 20 is a diagram illustrating timing of image data of each portion of the fluorescent endoscopic device in FIG. 13.
Figure 21:
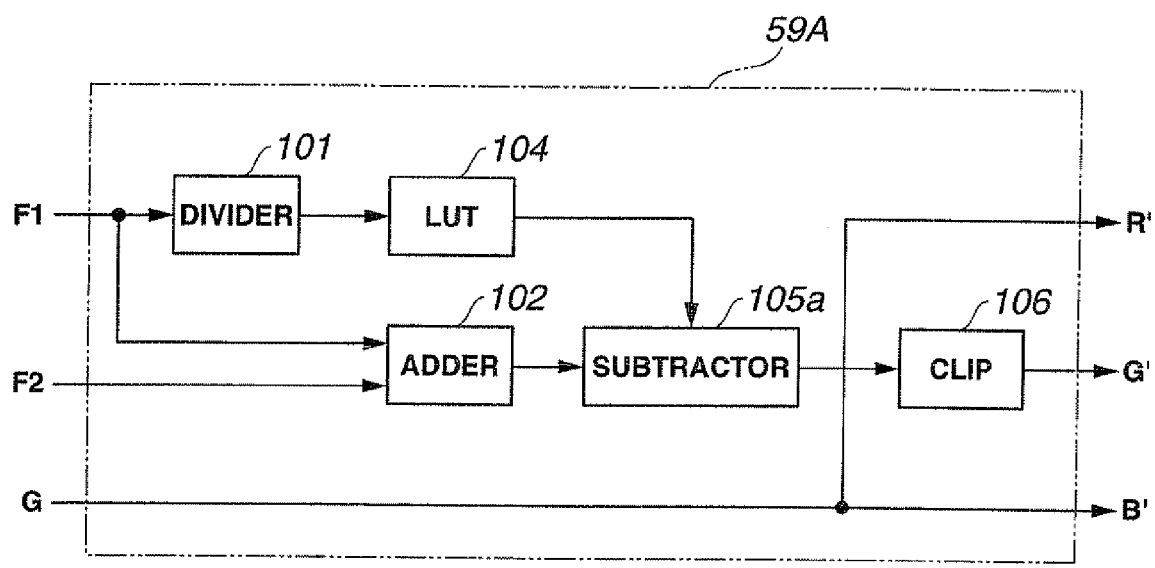
FIG. 21 is a block diagram illustrating configuration of an inter-image calculation portion in a first variation of the fluorescent endoscopic device in FIG. 13.
Figure 22:
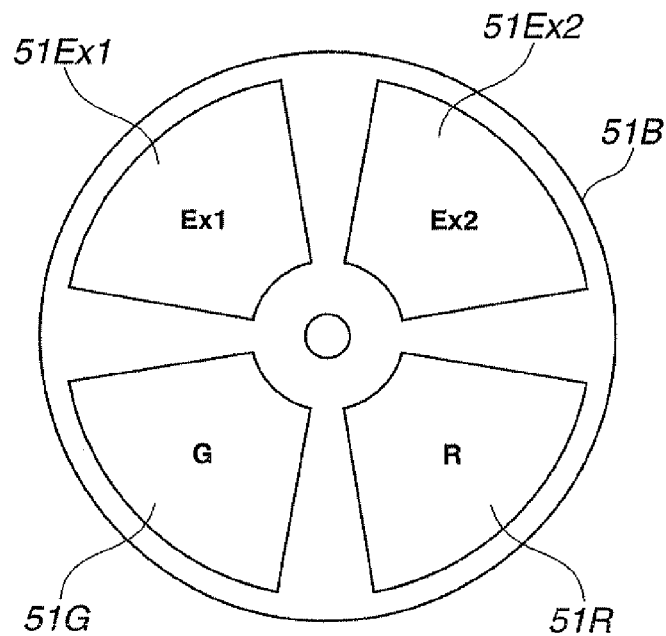
FIG. 22 is a diagram illustrating configuration of a rotating filter in a second variation of the fluorescent endoscopic device in FIG. 13.
Figure 23:
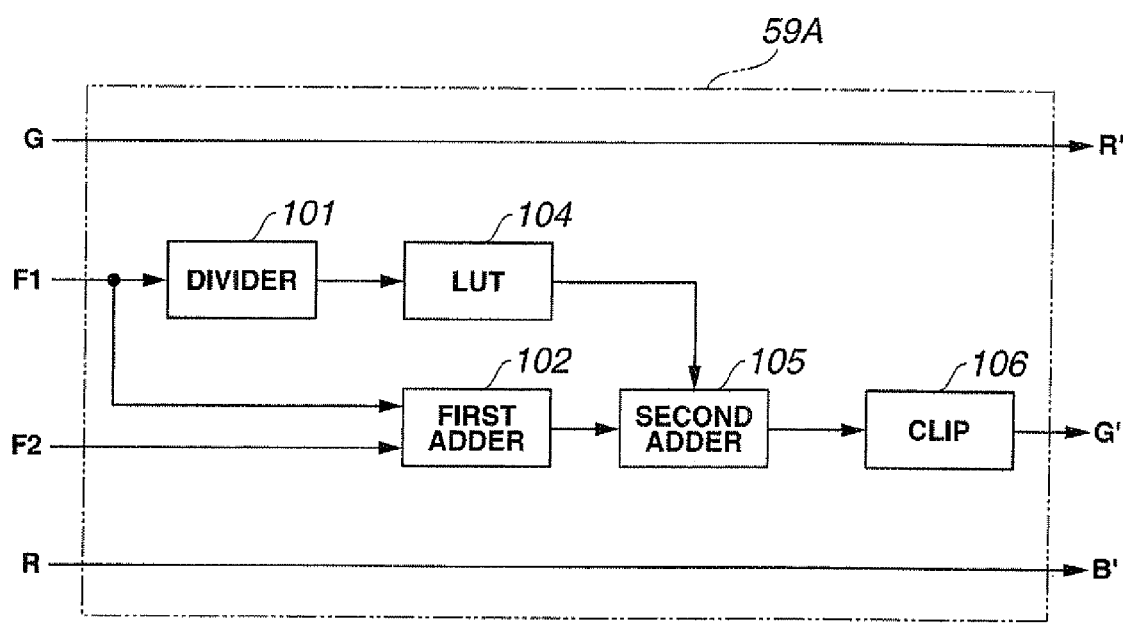
FIG. 23 is a block diagram illustrating configuration of the inter-image calculation portion in the second variation of the fluorescent endoscopic device in FIG. 13.

FIGS. 13 to 23 relate to an embodiment 2 of the present invention, in which FIG. 13 is a configuration diagram illustrating configuration of a fluorescent endoscopic device, FIG. 14 is a diagram illustrating configuration of the rotating filter in FIG. 13, FIG. 15 is a diagram illustrating a transmission characteristic of a G filter in FIG. 14, FIG. 16 is a diagram illustrating a transmission characteristic of an EX1 filter and an EX2 filter in FIG. 14, FIG. 17 is a diagram illustrating a transmission characteristic of an excitation light cut filter in FIG. 13, FIG. 18 is a diagram for explaining an action of a fluorescent endoscopic device in FIG. 13, FIG. 19 is a block diagram illustrating configuration of an inter-image calculation portion in FIG. 13, FIG. 20 is a diagram illustrating timing of image data of each portion of the fluorescent endoscopic device in FIG. 13, FIG. 21 is a block diagram illustrating configuration of an inter-image calculation portion in a first variation of the fluorescent endoscopic device in FIG. 13, FIG. 22 is a diagram illustrating configuration of a rotating filter in a second variation of the fluorescent endoscopic device in FIG. 13, FIG. 23 is a block diagram illustrating configuration of the inter-image calculation portion in the second variation of the fluorescent endoscopic device in FIG. 13.

Since the embodiment 2 is substantially the same as the embodiment 1, only different points will be explained, but the same reference numerals are given to the same configuration and the description will be omitted.

In the present embodiment 2, as shown in FIG. 13, a CCD 29a is a monochrome CCD and is driven by a CCD driving signal from the CCD driving circuit 31 provided in a video processor 4A and photoelectrically converts an optical image formed by the CCD 29 and outputs an image signal.

The image signal is amplified by a pre-amplifier 152 provided in the video processor 4A and further amplified to a predetermined level by an auto gain control (AGC) circuit 153 and then, converted by the A/ID conversion circuit 54 from an analog signal to a digital signal (image data), and each image data is temporarily stored in a first frame memory 156a, a second frame memory 156b, and a third frame memory 156c through a multiplexer 155 for switching.

The control circuit 15 controls the switching of a multiplexer 35 so that the each picked-up image data is sequentially stored in the first frame memory 156a, the second frame memory 156b, and the third frame memory 156c.

The image data stored in the frame memories 156a to 156c are inputted to an inter-image calculation portion 59A, a calculation processing, which will be described later, for making inputted signals correspond to color signals of the R, G, B channels is performed in the inter-image calculation portion 59A and converted to an analog RGB signal by a D/A conversion circuit 61 and outputted to the monitor 5.

A rotating filter 51A of the present embodiment is, as shown in FIG. 14, constituted by a G filter 51G transmitting G light (transmission characteristics thereof is shown in FIG. 15), an EX1 filter 51EX1 transmitting first excitation light and an EX2 filter 51EX2 transmitting second excitation light (transmission characteristics thereof are shown in FIG. 16). An excitation light cut filter 30 for cutting off the excitation light in the present embodiment has a transmission characteristic as shown in FIG. 17 and transmits G reflection light, which is return light when the G light is irradiated to a living tissue.

As shown in FIG. 18, a shallow tissue 160 and a deep tissue 161 have different excitation light wavelengths promoting auto-fluorescence in a living tissue. Then, in the present embodiment, optical images by auto-fluorescence F1, F2 from the tissues with different depths are picked up by irradiating the excitation light EX1, EX2 with the characteristics as shown in FIG. 16 to the living tissue and an optical image by the reflection light of the G light by the G filter 51G is picked up. The frame memories 156a to 156c temporarily store the three image data (F1, F2, G).

The inter-image calculation portion 59A includes the divider 101, the LUT 104, the first adder 102, the second adder 105, and the clip portion 106 for executing the calculation processing to the three image data (F1, F2, G) from frame memories 36a to 36c as shown in FIG. 19.

The action of the present embodiment configured as above will be described. Calculations shown in the following formula (6) are executed for the image data (F1, F2, G) at each of the divider 101, the first adder 102, the second adder 105, the LUT 104, and the clip portion 106, and the results are outputted as the image data (R', G', B');

$$R' = G$$

$$G' = F1 + F2 + K \log_2(F1/F2)$$

$$B' = G \qquad (6)$$

Specifically, as shown in FIG. 20, the inter-image calculation portion 59A inputs F1 image data from the frame memory 156a (hereinafter referred to as F1) and the F2 image data from the frame memory 156b (hereinafter referred to as F2) to the divider 101 and the first adder 102.

The first divider 101 executes the calculation of "F1/F2" for each pixel. At the subsequent LUT 104, the calculation of the logarithmic arithmetic and multiplication of the coefficient K is executed to the output of the divider 101 by referring to a table.

The first adder 102 adds F1 and F2, while the subsequent second adder 105 adds the output of the LUT 104 to the output of the first adder 102.

The first clip portion 106 executes clip processing to the output of the second adder 105 in a case where predetermined bit accuracy is exceeded and outputs the result as the image data G', which is a G-channel output of the inter-image calculation portion 59A, to the D/A conversion circuit 61.

The inter-image calculation portion 59A outputs the G image data from the frame memory 156c (hereinafter referred to as G) as the image data R', which is an R-channel output of the inter-image calculation portion 59A, and the image data B', which is a B-channel output, to the D/A conversion circuit 61.

The clip portion 106 delays the output of the image data G' for a predetermined time according to output timing of the image data R' and the image data B', synchronizes and outputs the image data R', the image data B', and the image data G'.

An effect of the division in the formula (6) will be explained. A pixel value IntF1 (i, j) at a position (i, j) of the fluorescent image by the excitation light Ex1 is defined by the following formula (7), and pixel value IntF2 (i, j) at a position (i, j) of the fluorescent image by the excitation light Ex2 is defined by the following formula (8);

$$IntF1(i, j) = IntEx1(i, j) \sum_{\lambda} ObjEx1(\lambda, i, j) Sens(\lambda) \qquad (7)$$

$$IntF2(i, j) = IntEx2(i, j) \sum_{\lambda} ObjEx2(\lambda, i, j) Sens(\lambda) \qquad (8)$$

where

IntEx1(i, j) is intensity at the position (i, j) of the excitation light EX1,

ObjEx1($\lambda$, i, j) is a comprehensive response characteristic of a mucous considering concentrations and fluorescence quantum yield of endogenous fluorescent substances and dispersion and absorbing characteristics of the excitation light and the fluorescence corresponding to the excitation light Ex1, Sens ($\lambda$) is a comprehensive spectral product of an image pickup system in which spectral transmittance of the objective lens and a spectral sensitivity of the image pickup device are combined, and IntEx2(i, j) is intensity at the position (i, j) of the excitation light Ex2, ObjEx2($\lambda$, i, j) is a comprehensive response characteristic of a mucous considering concentrations and fluorescence quantum yield of endogenous fluorescent substances and dispersion and absorbing characteristics of the excitation light and the fluorescence corresponding to the excitation light Ex2, $\lambda$ is a fluorescence detection wavelength band.

If the spectral characteristics of the illumination system are designed to be equivalent for the wavelength bands of the excitation lights Ex1 and Ex2, a relation as shown in the formula (9) is obtained:

$$IntEx1(i,j) = ItEx2(i,j) \qquad (9)$$

That is, if the formula (9) is satisfied, the following is derived:

$$\frac{IntF1(i, j)}{IntF2(i, j)} = \frac{\sum_{\lambda} ObjEx1(\lambda, i, j) 1 Sens(\lambda)}{\sum_{\lambda} ObjEx2(\lambda, i, j) Sens(\lambda)} \qquad (10)$$

and by taking a ratio between IntF1 and IntF2 from the relation in the formula (10), illumination intensity of the excitation light changed according to a position can be cancelled.

Subsequently, an effect of logarithmic arithmetic in the formula (6) will be described. In F1/F2, if the relation of the pixel values (position (i,j)) of the fluorescent image is F1(i, j)>F2(i, j), the logarithmic component becomes a positive value, while in the case of F1(i, j)<F2(i, j), the component becomes a negative value. By acquiring logarithm, contrast change can be added onto the image data in which F1 and F2 are added together according to the magnitude of F1 and F2, without being affected by the illumination intensity of the excitation light (changed according to the position).

Thus, it becomes possible to improve brightness of the fluorescent image and to create image information reflecting a difference in fluorescent substances to be excited and a difference in their distribution layers.

In the present embodiment, too, as mentioned above, the effect similar to that in the embodiment 1 can be obtained.

(Variation)

First Variation

As a first variation of the inter-image calculation portion 59A of the embodiment 2, as shown in FIG. 21, it may be so configured that the subtractor 105a is used instead of the second adder 105. The calculation by the inter-image calculation portion 59A in this case is as in the formula (11):

$$R'=G$$

$$G'=F1+F2-K \log_2(F2/F1)$$

$$B'=G \quad (11)$$

In the first variation, too, the actions/effects similar to those in the present embodiment can be obtained.

Second Variation:

As a second variation of the embodiment 2, it may be so configured that a rotating filter 51B as shown in FIG. 22 may be provided instead of the rotating filter 51A. The rotating filter 51B is constituted by an R filter 51R transmitting R light in addition to the G filter 51G, the EX1 filter 51EX1, and EX2 filter 51EX2.

In the second variation, a fourth frame memory for storing an optical image by reflection light of reference light R in an R light band by means of the R filter 51R is provided in addition to the three frame memories 156a to 156c in the video processor 4A, though not shown.

Furthermore, as shown in FIG. 23, the inter-image calculation portion 59A of the second variation outputs G image data from the frame memory 156c as the image data R', which is an R-channel output, and the R image data from the fourth frame memory as the image data B', which is a B-channel output, to the D/A conversion circuit 61. The calculation by the inter-image calculation portion 59A in this case is as in the formula (12):

$$R'=G$$

$$G'=F1+F2+K \log_2(F1/F2)$$

$$B'=R \quad (12)$$

In the second variation, too, the actions/effects similar to those in the present embodiment can be obtained.

The present invention is not limited to the above-mentioned embodiments but is capable of various changes, alterations and the like in a range not changing the gist of the present invention.

What is claimed is:

1. A fluorescent endoscopic device, comprising:
an irradiation portion for irradiating illumination light and excitation light to a subject;
a light receiving portion for receiving a reflection light image generated from the subject on the basis of the illumination light, and a first fluorescent image and a second fluorescent image in a wavelength band different from a wavelength band of the first fluorescent image, which are generated from the subject on the basis of the excitation light;
a calculation portion for executing addition processing of the first fluorescent image and the second fluorescent image, division processing of the first fluorescent image and the second fluorescent image, logarithmic arithmetic processing of a result of the division processing, and processing of adding a result of the addition processing to a result of the logarithmic arithmetic processing or subtracting the result of the logarithmic arithmetic processing from the result of the addition processing; and
an image creation portion for creating a fluorescent observation image on the basis of the reflection light image by means of the illumination light, the first fluorescent image, the second fluorescent image and a processing result of the calculation portion.

2. The fluorescent endoscopic device according to claim 1, wherein
the first fluorescent image and the second fluorescent image are fluorescent images on the basis of fluorescence in a green band and a red band excited by excitation light in a single wavelength band.

3. The fluorescent endoscopic device according to claim 1, wherein the excitation light by means of the irradiation portion includes first excitation light having a first wavelength band, and second excitation light having a second wavelength band different from the first wavelength band; and
the first fluorescent image is on the basis of the first excitation light, while the second fluorescent image is on the basis of the second excitation light.

4. The fluorescent endoscopic device according to claim 1, further comprising
a display portion for displaying a fluorescent observation image created by the image creation portion.

5. The fluorescent endoscopic device according to claim 1, wherein the first fluorescent image received by the light receiving portion is an image of a G channel of an RGB color image signal and the second fluorescent image is an image of an R channel of the RGB color image signal, and the result of the division processing is a value obtained by dividing a pixel value of the image of the G channel by a pixel value of the image of the R channel.

6. The fluorescent endoscopic device according to claim 4, wherein the first fluorescent image received by the light receiving portion is an image of a G channel of an RGB color image signal and the second fluorescent image is an image of an R channel of the RGB color image signal, and the result of the division processing is a value obtained by dividing a pixel value of the image of the G channel by a pixel value of the image of the R channel, and
an image of an R channel of the reflection light image is assigned to a B channel of R, G, B channels of the display portion, and the processing result of the calculation portion is assigned to a G channel of the R, G, B channels of the display portion, and a result of division processing of an image of a G channel of the reflection light image and an image of a B channel of the reflection light image is assigned to an R channel of the R, G, B channels of the display portion, to be inputted to the display portion.

7. The fluorescent endoscopic device according to claim 4, wherein the reflection light image is assigned to an R channel and a B channel of R, G, B channels of the display portion, and the processing result of the calculation portion is assigned to a G channel of the R, G, B channels of the display portion, to be inputted to the display portion.

8. The fluorescent endoscopic device according to claim 4, wherein an image in a first wavelength band of the reflection light image is assigned to an R channel of R, G, B channels of the display portion, an image in a second wavelength band different from the first wavelength band of the reflection light image is assigned to a B channel of the R, G, B channels of the display portion, and the processing result of the calculation portion is assigned to a G channel of the R, G, B channels of the display portion, to be inputted to the display portion.

9. A method of creating a fluorescent endoscopic image, comprising steps of:
    irradiating illumination light and excitation light from an irradiation portion;
    receiving a reflection light image on the basis of the illumination light, and a first fluorescent image and a second fluorescent image in a wavelength band different from a wavelength band of the first fluorescent image on the basis of the excitation light;
    executing addition processing of the first fluorescent image and the second fluorescent image, division processing of the first fluorescent image and the second fluorescent image, logarithmic arithmetic processing of a result of the division processing, and processing of adding a result of the addition processing to a result of the logarithmic arithmetic processing or subtracting the result of the logarithmic arithmetic processing from the result of the addition processing; and
    creating a fluorescent observation image on the basis of the reflection light image by means of the illumination light, the first fluorescent image, the second fluorescent image, and a processing result of the calculation processing.

10. The method of creating a fluorescent endoscopic image according to claim 9, wherein the first fluorescent image received by the light receiving portion is an image of a G channel of an RGB color image signal and the second fluorescent image is an image of an R channel of the RGB color image signal, and the result of the division processing is a value obtained by dividing a pixel value of the image of the G channel by a pixel value of the image of the R channel.

11. The method of creating a fluorescent endoscopic image according to claim 10, wherein an image of an R channel of the reflection light image is assigned to a B channel of R, G, B channels of a display portion for displaying the created fluorescent observation image, and the processing result of the calculation portion is assigned to a G channel of the R, G, B channels of the display portion, and a result of division processing of an image of a G channel of the reflection light image and an image of a B channel of the reflection light image is assigned to an R channel of the R, G, B channels of the display portion, to be inputted to the display portion.

12. The method of creating a fluorescent endoscopic image according to claim 9, wherein the reflection light image is assigned to an R channel and a B channel of R, G, B channels of a display portion for displaying the created fluorescent observation image, and the processing result of the calculation portion is assigned to a G channel of the R, G, B channels of the display portion, to be inputted to the display portion.

13. The method of creating a fluorescent endoscopic image according to claim 9, wherein an image in a first wavelength band of the reflection light image is assigned to an R channel of R, G, B channels of a display portion for displaying the created fluorescent observation image, an image in a second wavelength band different from the first wavelength band of the reflection light image is assigned to a B channel of the R, G, B channels of the display portion, and the processing result of the calculation portion is assigned to a G channel of the R, G, B channels of the display portion, to be inputted to the display portion.

* * * * *